United States Patent [19]
Allen et al.

[11] Patent Number: 6,165,777
[45] Date of Patent: *Dec. 26, 2000

[54] **PROCESS FOR THE RESOLUTION OF CIS 1, 2-INDANE DIOLS USING *PSEUDOMONAS PUTIDA***

[75] Inventors: Christopher Curtis Royston Allen; Derek Raymond Boyd, both of Belfast; Howard Dalton, Long Itchington, all of United Kingdom

[73] Assignee: Zeneca Limited, London, United Kingdom

[ * ] Notice: This patent is subject to a terminal disclaimer.

[21] Appl. No.: 09/093,875

[22] Filed: Jun. 9, 1998

Related U.S. Application Data

[63] Continuation of application No. 08/817,108, filed as application No. PCT/GB95/02051, Aug. 31, 1995, Pat. No. 5,811,294.

[30] Foreign Application Priority Data

Oct. 5, 1994 [GB] United Kingdom .................. 9420067

[51] Int. Cl.[7] ............................. C07C 00/00; C12P 41/00
[52] U.S. Cl. ............................. 435/280; 435/877
[58] Field of Search ...................... 435/280, 877

[56] References Cited

U.S. PATENT DOCUMENTS

| | | | |
|---|---|---|---|
| 5,811,294 | 9/1998 | Allen et al. | 435/280 |
| 5,858,737 | 1/1999 | Buckland et al. | 435/129 |

OTHER PUBLICATIONS

Boyd et al: Stereospecific Benzylic Hydroxylation of Bicyclic Alkenes by *Pseudomonas putida*: Isolation of (+)–R–1–Hydroxy–1,2–dihydronaphthalene, an Arene Hydrate of Naphthalene from Metabolism of 1,2–Dihydronaphthalene, Journal of the Chemical Society, Chemical Communications, No. 6, 1989, pp. 339–340.

Wackett et al: "Benzylic monooxygenation catalyzed by Toluene monooxygenase from *Pseudomonas putida*", Biochemistry, vol. 27, No. 4, Feb. 23, 1988 pp. 1360–1367.

Boyd et al: "Stereodirecting substituent effects during enzyme–catlysed sunthesis of cis–dihydrodiol metabolites, og 1,4–Disubstituted benzene substrates", Journal of the Chemical Society, Chemical Communications, No. 11, Jun. 7, 1993, pp. 974–976.

Allen et al: "Enantioselective bacterial biotransformation routes to cis–diol metabolites of monosubstituted benzenes, naphthalene and bensocycloalkenes of either absolute configuration", Journal of the Chemical Society, Chemical Communictions, No. 2, Jan. 21, 1995, pp. 117–119.

Jones, JB, "Enzymes in Organic Synthesis", Tetrahedron, 42:3351–3403 (1986).

*Primary Examiner*—Sandra E. Saucier
*Attorney, Agent, or Firm*—Pillsbury Madison & Sutro LLP

[57] ABSTRACT

A process for resolution of a mixture of dihydroxydihydroindene enantiomers comprising treating the mixture of enantiomers with a *Pseudomonas putida* species microorganism.

Resolved dihydroxydihydroindenes are valuable intermediates for the synthesis of biologically active compounds such as pharmaceuticals and agrochemicals.

8 Claims, No Drawings

PROCESS FOR THE RESOLUTION OF CIS 1, 2-INDANE DIOLS USING *PSEUDOMONAS PUTIDA*

This is a continuation of application No. 08/817,108 filed Apr. 4, 1997, now U.S. Pat. No. 5,811,294.

This application is a continuation of 08/817,108 which is a 371 of PCT GB95/02051 filed Aug. 31, 1995.

This invention relates to a process for the resolution of racemic diols, particularly to a process for the resolution of racemic cis-diols and especially to a process for the resolution of racemic aromatic, alicylic and heterocyclic cis-diols particularly dihydroxydihydroindenes and more particularly vicinal cis dihydroxydihydroindenes.

Resolved dihydroxydihydroindenes are valuable intermediates for the synthesis of biologically active compounds such as pharmaceuticals and agrochemicals.

It has now been found that resolved diols, particularly dihydroxydihydroindenes, more particularly vicinal cis dihydroxydihydroindenes may be conveniently prepared in high enantiomeric excess (e.e.) in good overall yield via biotransformations using appropriate microorganisms.

According to the present invention there is provided a process for resolution of a mixture of dihydroxydihydroindene enantiomers comprising treating the mixture of enantiomers with a *Pseudomonas putida* species microorganism.

The mixture of dihydroxydihydroindene enantiomers preferably comprises compounds of the general Formula (1):

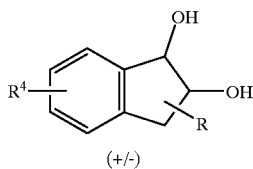

Formula (1)

(+/-)

in which R and $R^4$ each independently is —H, halogen, —$N_3$, —OH, —CN, alkyl, alkenyl, aryl, —$CX_3$, —$OR^1$, —$SR^1$, —$NR^1R^2$, —$PR^1R^2$, —$COR^1$, —$CO_2R^1$, in which X is halogen, and $R^1$ and $R^2$ each independently is alkyl, aryl, alkenyl or aralkyl.

Each of the alkyl, alkenyl, aryl and aralkyl groups represented by R, $R^1$, $R^2$ and $R^4$ may be optionally substituted by substituents selected from —$NO_2$, —CN, —F, —Cl, —Br, —I, —$C_{1-6}$-alkyl, —$C_{1-6}$-alkoxy, —$CF_3$, —OH, —$OR^3$ in which $R^3$ is alkyl, aryl, alkenyl or aralkyl.

Where one of R, $R^1$, $R^2$, $R^3$ or $R^4$ is alkyl it is preferably $C_{1-10}$-alkyl, more preferably $C_{1-6}$-alkyl and especially $C_{1-4}$-alkyl.

Where one of R, $R^1$, $R^2$, $R^3$ or R is alkenyl it is preferably $C_{2-10}$-alkenyl, more preferably $C_{2-6}$-alkenyl. Where one of R, $R^1$, $R^2$, $R^3$ or $R^4$ is aryl it is preferably phenyl.

Where one of $R^1$, $R^2$ or $R^3$ is aralkyl it is preferably $C_{1-6}$-alkylphenyl more preferably benzyl.

R and $R^4$ each independently is preferably —H, —F, —Cl, —Br, —I, —$N_3$, —OH, —CN, alkyl, alkenyl, aryl, —$CX_3$, —$OR^1$, —$SR^1$ or —$COR^1$ in which X is halogen and $R^1$ is alkyl, aryl, alkenyl or aralkyl, more preferably —H, —F, —Cl, —Br, —I, —$N_3$, —OH, —CN, $C_{1-6}$-alkyl, $C_{2-6}$-alkenyl, phenyl, —$CF_3$, —$CCl_3$, —$OC_{1-6}$-alkyl, —$SC_{1-6}$-alkyl or —$COC_{1-6}$-alkyl; and especially —H, —F, —Cl, —Br, —I, —$N_3$, —OH, —CN, —$CH_3$, —$C_2H_5$, —$OCH_3$, —$SCH_3$ or —$COCH_3$.

The compound of Formula (1) is preferably of Formula (2):

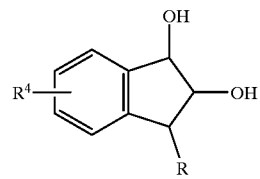

Formula (2)

in which R and $R^4$ are as hereinbefore defined.

Especially preferred compounds of Formulae (1) and (2) are those in which R is as hereinbefore defined and $R^4$ is —H, alkyl or alkoxy.

Where R is a substituent other than —H the carbon atom to which R is attached is a chiral centre. The present process provides a means of resolving dihydroxydihydroindenes which have three chiral centres at the 1-, 2- and 3-positions of the 5 membered ring and accordingly forms a further feature of the present invention.

Where one of R, $R^4$ or X is halogen it is preferably —F, —Cl, —Br or —I, more preferably —F, —Cl or —Br.

The process is preferably performed in an aqueous medium, more preferably in a buffered aqueous medium. Suitable buffers may be inorganic or organic and are preferably those which control the pH of the medium in the range 4 to 9, more preferably in the range 6 to 8, and especially at a pH of 7. The buffer is preferably inorganic, more preferably an alkali metal phosphate, especially potassium phosphate. A particularly suitable aqueous medium is 0.1 M potassium phosphate.

A co-substrate which provides for NADH (nicotinamide adenine dinucleotide) recycle may optionally be added to the aqueous medium. Preferred co-substrates are α-keto acids such as sodium pyruvate, and alcohols such as ethanol, isopropanol or glucose.

The process is preferably performed at a temperature from 0° C. to 1000° C., more preferably at from 20° C. to 45° C. and especially at from 28° C. to 32° C.

After reaction has proceeded for a suitable period which may be from a few hours to many days it may be terminated by any convenient means such as by removing the microorganism by centrifugation and/or cooling the reaction mass to less than 5° C.

The product may be isolated from the reaction mixture by solvent extraction using an ester such as ethylacetate. The product may be purified by any convenient means such as column chromatography for example by elution from Silica gel or Kieselgel C60 using methanol or mixtures of methanol and dichloromethane as eluent or by recrystallisation from an ester/alkane mixture such as ethylacetate/hexane.

The dihydroxydihydroindene mixture is preferably a mixture of and more preferably a racemic mixture of cis-dihydroxydihydroindene enantiomers. A preferred dihydroxydihydroindene mixture is one in which the dihydroxydihydroindenes are of general Formulae (1) or (2) and both R and $R^4$ are H. Selection of the *Pseudomonas putida* species allows the asymmetric destruction of one of the enantiomers. Thus in a first preferred embodiment of the present invention a mixture of cis-1,2-dihydroxy-1,2-dihydroindenes is treated with *Pseudomonas putida* NCIMB8859 to give cis-[1S:2R]-dihydroxy-1,2-dihydroindene.

In a second preferred embodiment of the present invention a mixture of cis-1,2-dihydroxydihydroindenes is treated with *Pseudomonas putida* NCIMB 11767 or NCIMB 12190 to give cis-[1R:2S]-dihydroxy-1,2-dihydroindene.

The present invention is further illustrated by the following examples:

EXAMPLE 1
Biotransformation with *Pseudomonas putida* NCIMB 8859

1. Source of microorganism

*Pseudomonas putida* NCIMB 8859 (hereinafter known as NCIMB 8859) was obtained as a freeze-dried culture from The National Collections of Industrial and Marine Bacteria Ltd., 23, St Machar Drive, Aberdeen, Scotland, AB2 1 RY.

2. Growth of strain NCIMB 8859

The NCIMB 8859 was grown on a defined minimal medium, with solid naphthalene added as carbon source. The minimal medium comprised:

| | |
|---|---|
| $KH_2PO_4$ | 0.96 g/l |
| $K_2HPO_4$ | 1.23 g/l |
| $NH_4Cl$ | 3.00 g/l |
| $MgSO_4.7H_2O$ | 0.40 g/l |
| Trace elements solution | 1.9 ml/l |

The trace elements solution comprised:

| | |
|---|---|
| $Na_2EDTA$ | 50.00 g/l |
| $ZnSO_4.7H_2O$ | 2.20 g/l |
| $CaCl_2$ | 5.54 g/l |
| $MnCl_2.4H_2O$ | 5.06 g/l |
| $FeSO_4.7H_2O$ | 5.00 g/l |
| $(NH_4)_6Mo_7O_{24}.4H_2O$ | 1.10 g/l |
| $CuSO_4.5H_2O$ | 1.57 g/l |
| $CoCl_2.6H_2O$ | 1.61 g/l |

Components were dissolved into solution in the order shown above. The pH was adjusted to pH 6.0 with 2M KOH after addition of the EDTA salt, and after addition of the last component.

After sterilisation, 2g/l of naphthalene was added to the minimal medium as a sole carbon source. Cultures were inoculated with either a single colony from agar plates or with a naphthalene grown liquid culture of strain NCIMB 8859.

The NCIMB 8859 was grown in 21 shakeflasks containing 400 ml of minimal medium in batch culture at 30° C. on an orbital shaker (300 rpm). Before use for biotransformations the NCIMB 8859 mixture was harvested in the late-exponential phase of growth and initially filtered through glass wool to remove excess naphthalene.

3. Preparation of racemic (1R:2S/1S:2R)-1,2-dihydroxy-1,2-dihydroindene

To a stirred solution of indene (0.5 g, 4.3 m mol), in a mixture of water (2.5 cm³ acetone (5 cm³) and tert-butanol (1.5 cm³), was added 4-methylmorpholine-N-oxide (0.6 g, 5.9 mmol) and a solution of osmium tetroxide in carbon tetrachloride (0.005 g/0.5 cm³). After stirring the reaction mixture for three days, at ambient temperature, a saturated aqueous solution of sodium metabisulphite (0.5 cm³) was added and the stirring was continued for another hour. The reaction mixture was diluted with water (50 cm³), extracted with ethyl acetate (2×50 cm³) and dried ($Na_2SO_4$). Distillation of the solvent, from the organic extract, under reduced pressure, gave crude racemic (1R:2S/1S:2R) 1,2-dihydroxy-1,2-dihydroindene as off-white fluffy crystals (0.63 g, 97%) m.pt. 98°–100° C.

4. Biotransformation of racemic cis-1,2-dihydroxy-1,2-dihydroindene.

The NClMB 8859 mixture obtained after Step 2 (above) was centrifuged (8k rpm, 15 min, 25° C.) to obtain a cell pellet. The bacterial cells were then resuspended in 0.1M potassium phosphate buffer (pH 7.0) to give a final optical density at 600nm of 3.08. The racemic cis-1,2-dihydroxy-1,2-dihydroindene substrate (which had been dissolved in the buffer) was then added to the reaction mixture to give a final concentration of 0.42 g/l.

Sodium pyruvate was added as a cosubstrate. To a 380 cm³ reaction volume, 15.2 cm³ of a 10% sodium pyruvate solution was added to give a final concentration of 35 mM.

The biotransformation mixture (395.2 cm³) was incubated at 30° C. in a 21 shakeflask, on an orbital shaker (300 rpm) for 24 hours. At the end of this period the reaction was terminated by centrifugation (8k rpm, 15 minutes, 4° C.) and the supernatant liquor was stored at 4° C. prior to product purification.

5. Product purification

The supernatant liquor from 4 above was concentrated to one fifth of its volume under reduced pressure and the concentrate was saturated with sodium chloride. The saturated solution was extracted twice with ethylacetate (2×80 cm³) and the combined extract was dried over anhydrous sodium sulphate before evaporating to dryness. The crude product was recrystallised from ethylacetate/hexane to give cis-[1S:2R]-dihydroxy-1,2dihydroindene (35%, >98% e.e.) (The e.e. value was obtained by the $^1$H-NMR analysis of the dimethylterephthalic acid ester derivatives and chiral stationary phase HPLC).

6. Biotransformation of racemic 3-substituted cis-1,2-dihydroxy-1,2-dihydroindenes Separate partial kinetic resolutions of the racemic substrates, [1S:2R:3R/1R:2S:3S]-3-methyl-cis-1,2-dihydroxy-1,2-dihydroindene or [1S:2R:3S1R:2S:3R]-3-methyl-cis-1,2-dihydroxy-1,2-dihydroindene (obtained by 0504 oxidation of the corresponding alkene, 1-methylindene were carried out under similar conditions to those reported in Section 4 using *Pseudomonas putida* NCIMB 8859 but over a shorter biotransformation period (16 h). The recovered substrates were in each case found to be enriched in one enantiomer i.e. the (–)-[1S:2R:3R] (50% e.e) and the (+)-[1S:2R:3S] (48% e.e) by chiral stationary phase HPLC analysis in yields of 30% and 54% respectively. Time—course studies of this enzyme-catalysed kinetic resolution procedure on racemic cis-1,2-dihydroxy-1,2-dihydroindene showed that given sufficient time and sufficiently high cell density, a total resolution could be achieved. No similar attempt has been made to optimize the kinetic resolution of either racemic substrates, [1S:2R:3R/1R:2S-3S]-3-methyl-cis-1,2-dihydroxy-1,2-dihydroindene or [1S:2R:3S/1R:2S:3R]-3-methyl-cis-1,2-dihydroxy-1,2-dihydroindene, and a total resolution will require the latter type of optimization.

What is claimed is:

1. A process for the resolution of a mixture of enantiomers of a cis-1,2-dihydroxydihydroindene compound of Formula (1):

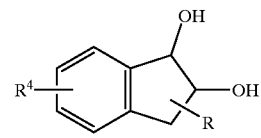

wherein R and $R^4$ each independently is —H, halogen, —$N_3$, —OH, —CN, alkyl, alkenyl, aryl, —$CX_3$, —$OR^1$, —$SR^1$, —$NR^1R^2$, —$PR^1R^2$, —$COR^1$, —$CO_2R^1$, in which X is halogen, and $R^1$ and $R^2$ each independently is alkyl, aryl, alkenyl or aralkyl comprising: treating a mixture of compounds of Formula (1) with *Pseudomonas putida* for a sufficient time to allow the destruction of the 1R,2S-enantiomer of Formula (1) and recovering the 1S,2R enantiomer of formula (1).

2. A process for the resolution of a mixture of enantiomers of a cis-1,2-dihydroxydihydroindene compound of Formula (2):

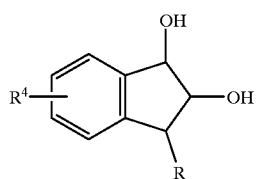

wherein R and $R^4$ each independently is —H, halogen, —$N_3$, —OH, —CN, alkyl, alkenyl, aryl, —$CX_3$, —$OR^1$, —$SR^1$, —$NR^1R^2$, —$PR^1R^2$, —$COR^1$, —$CO_2R^1$, in which X is halogen, and $R^1$ and $R^2$ each independently is alkyl, aryl, alkenyl or aralkyl comprising: treating a mixture of compounds of Formula (2) with *Pseudomonas putida* for a sufficient time to allow the destruction of the 1R,2S-enantiomer of Formula (2) and recovering the 1S,2R enantiomer of formula (2).

3. The process according to claim 1 or 2 in which the *Pseudomonas putida* species is selected from NClMB 8859, NClMB 11767 and NClMB 12190.

4. The process according to claim 1 in which the cis-dihydroxydihydroindene is cis-1,2-dihydroxy-1,2-dihydroindene and the *Pseudomonas putida* species is *Pseudomonas putida* NClMB 8859.

5. The process according to claim 1 in which the cis-dihydroxydihydroindene is cis-1,2-dihydroxy-1,2-dihydroindene and the *Pseudomonas putida* species is *Pseudomonas putida* NClMB 11767.

6. The process according to claim 1 in which the cis-dihydroxydihydroindene is cis-1,2-dihydroxy-1,2-dihydroindene and the *Pseudomonas putida* species is *Pseudomonas putida* NClMB 12190.

7. The process according to claim 1 or 2 performed in an aqueous buffer medium in which the pH is controlled in the range 4 to 9.

8. The process according to claim 1 or 2 in which the temperature is from 0° C. to 100° C.

\* \* \* \* \*